United States Patent
Park

(10) Patent No.: US 10,047,336 B2
(45) Date of Patent: Aug. 14, 2018

(54) ECO-FRIENDLY HELIOSTAT ODOR REMOVAL SYSTEM

(71) Applicant: KYUNGPOOK NATIONAL UNIVERSITY INDUSTRY-ACADEMIC COOPERATION FOUNDATION, Daegu (KR)

(72) Inventor: Cheol Woo Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 328 days.

(21) Appl. No.: 14/972,097

(22) Filed: Dec. 17, 2015

(65) Prior Publication Data

US 2016/0186119 A1 Jun. 30, 2016

(30) Foreign Application Priority Data

Dec. 31, 2014 (KR) .................. 10-2014-0195220

(51) Int. Cl.
*C12M 1/00* (2006.01)
*C12M 1/34* (2006.01)
(52) U.S. Cl.
CPC ............ *C12M 47/18* (2013.01); *C12M 41/12* (2013.01); *Y02P 20/59* (2015.11)

(58) Field of Classification Search
CPC ....... C12M 21/02; C12M 41/12; C12M 47/18
See application file for complete search history.

(56) References Cited

U.S. PATENT DOCUMENTS 4,192,583 A * 3/1980 Horton ................... F24J 2/1052
126/602
2010/0255458 A1* 10/2010 Kinkaid ................ C12M 21/02
435/3

FOREIGN PATENT DOCUMENTS

KR 10-2007-0116757 A 12/2007
KR 10-2010-0100010 A 9/2010

* cited by examiner

*Primary Examiner* — William H. Beisner
(74) *Attorney, Agent, or Firm* — Revolution IP, PLLC

(57) ABSTRACT

Provided is an eco-friendly heliostat odor removal system, including: a solar cell which collects sunlight to generate electricity; an effective microorganism activation and cultivation box which purifies inflow contaminated air using an effective microorganism cultivation solution accommodated in a housing; a sunlight tracker which rotates or moves the solar cell to track the sun in accordance with an altitude of the sun; a controller which controls the effective microorganism activation and cultivation box and the sunlight tracker; and a battery storing unit which stores the electricity generated in the solar cell. Therefore, the power is supplied in an eco-friendly manner using solar heat energy and contaminated air is efficiently removed from industrial sites or a region where other odor is continuously generated by the effective microorganism cultivation solution.

8 Claims, 6 Drawing Sheets

[FIG. 1]
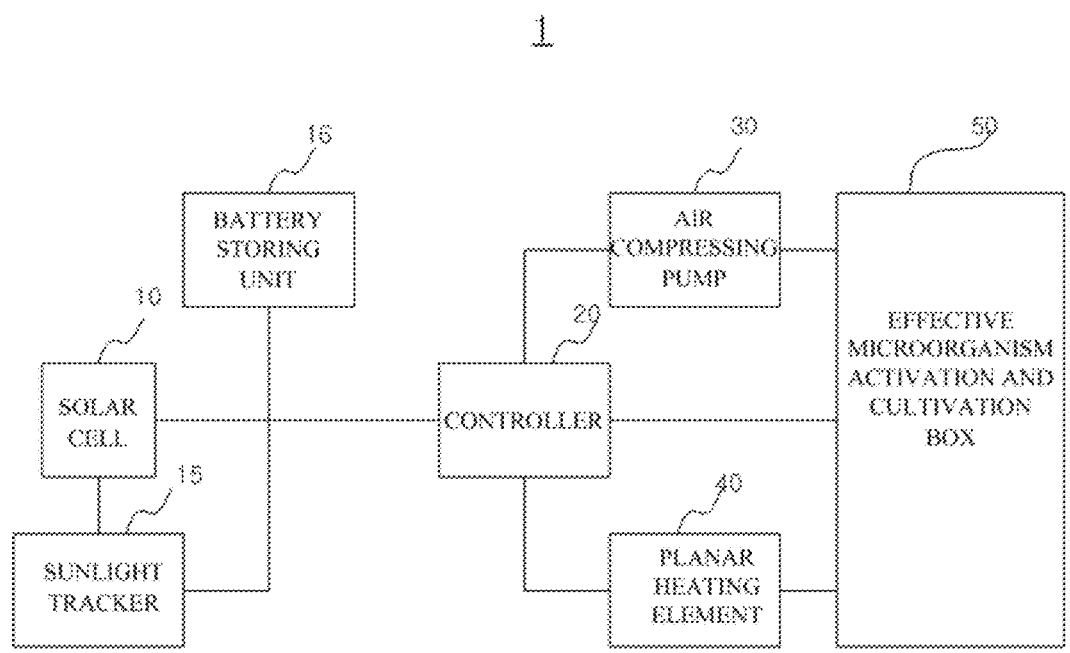

[FIG. 2]
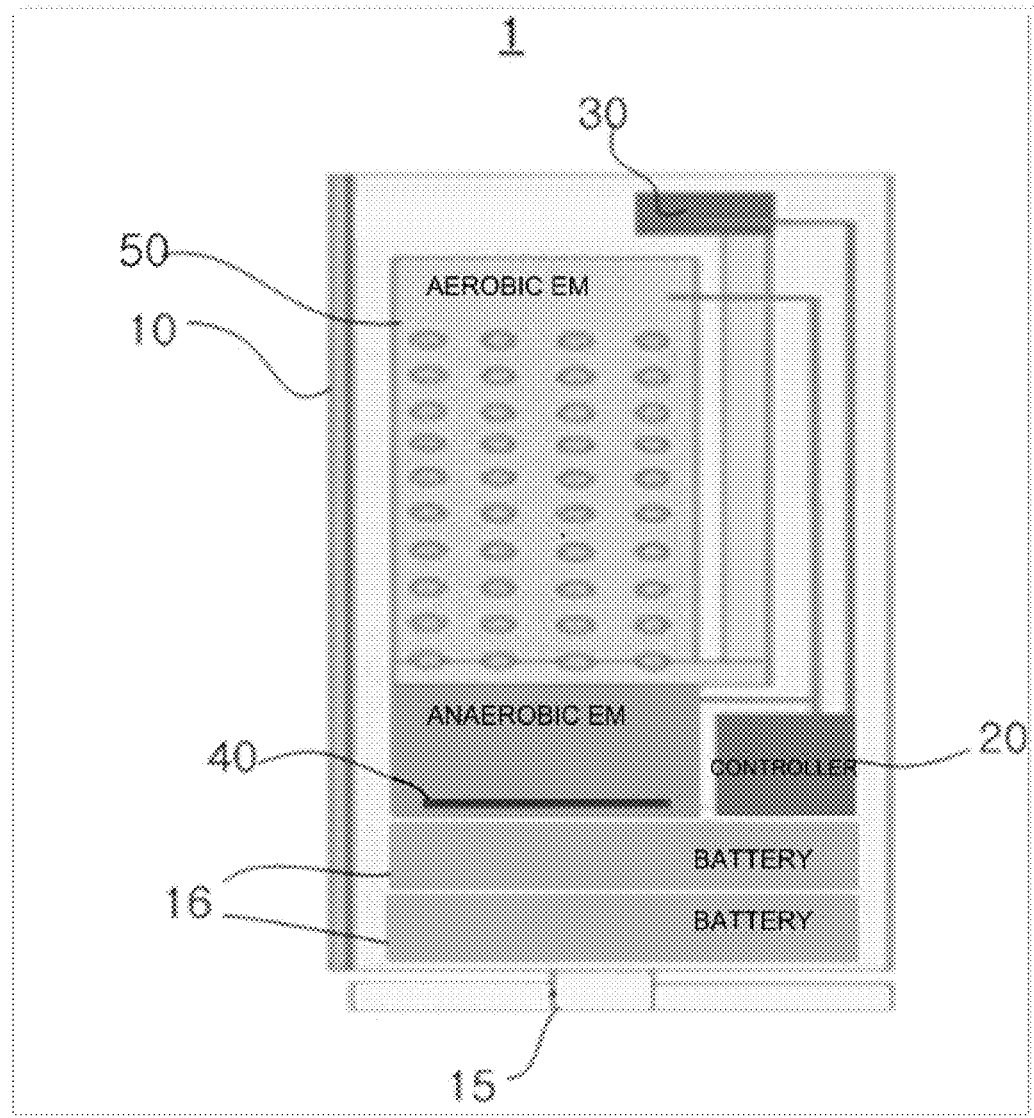

[FIG. 3]
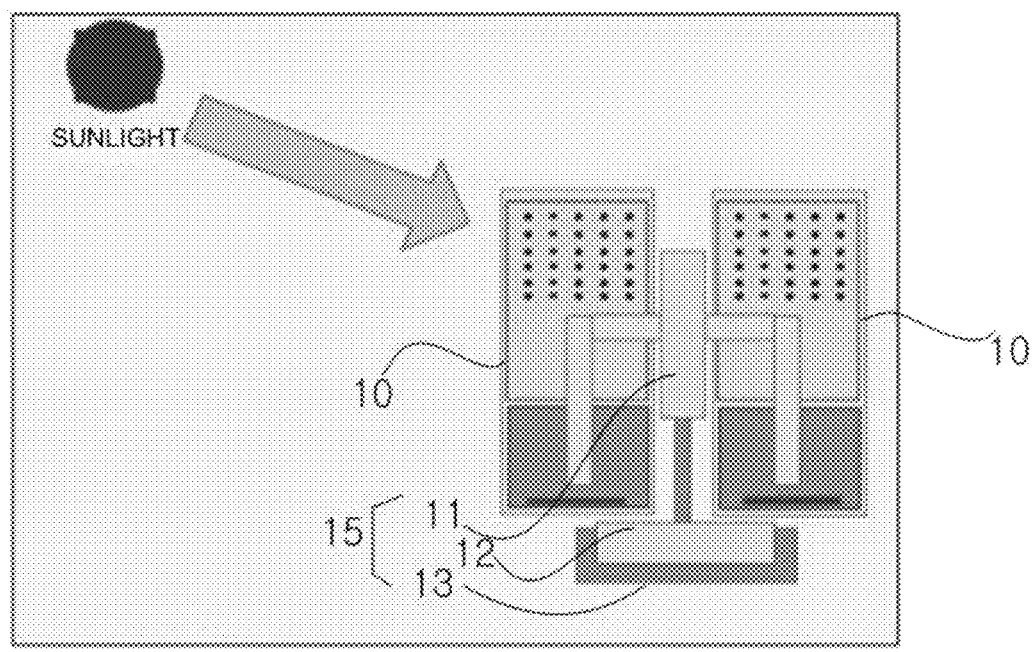

[FIG. 4]
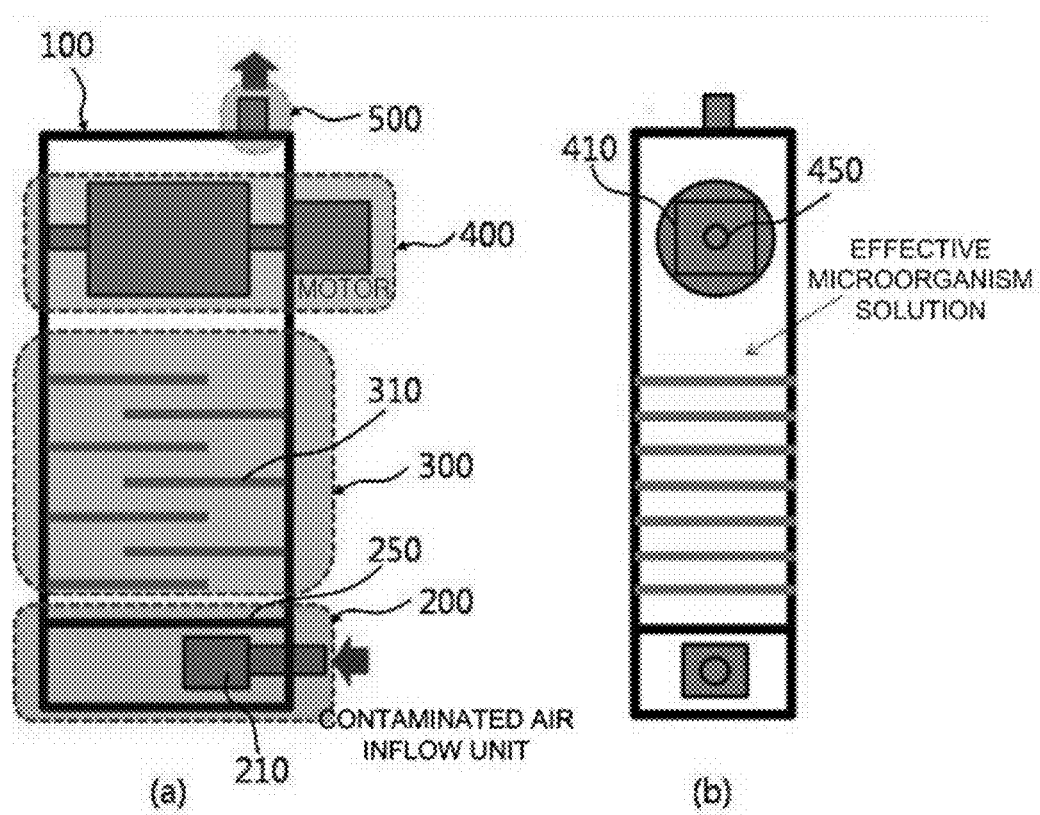

[FIG. 5]
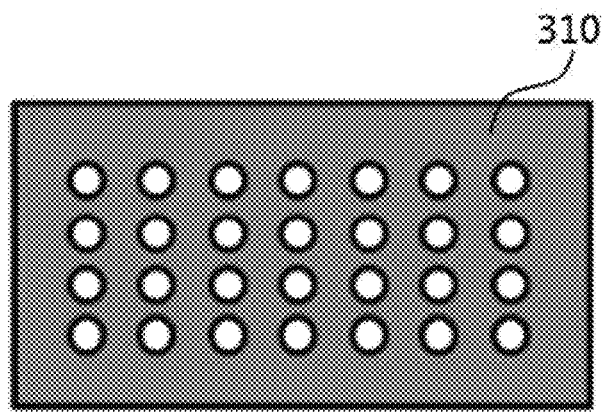
[FIG. 6]
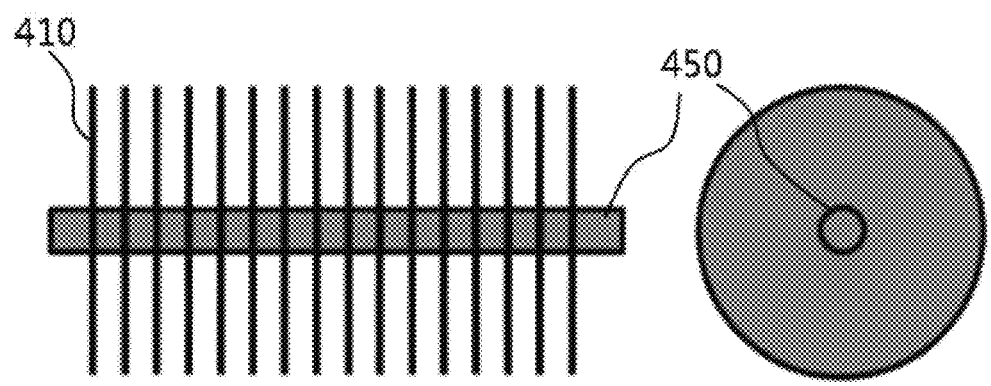

[FIG.7]
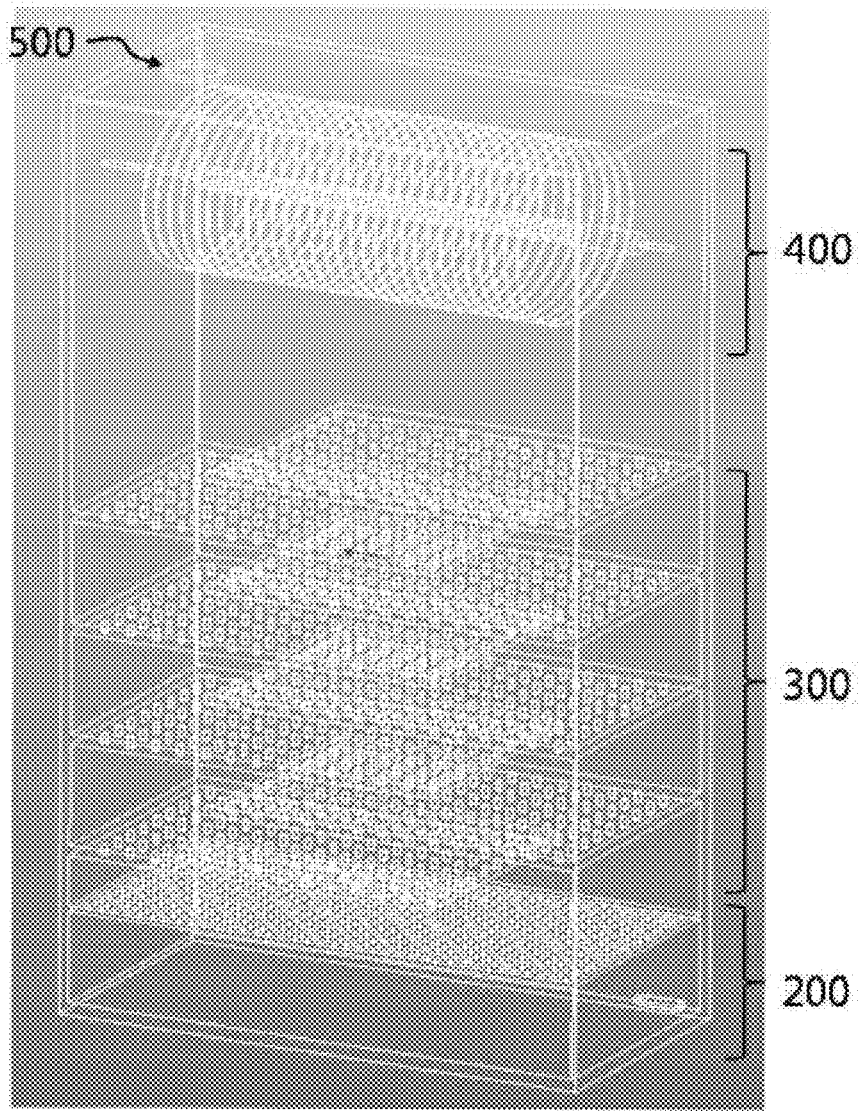

ECO-FRIENDLY HELIOSTAT ODOR REMOVAL SYSTEM

CROSS-REFERENCE TO RELATED APPLICATIONS

This application claims priority to and the benefit of Korean Patent Application No. 10-2014-0195220 filed in the Korean Intellectual Property Office on Dec. 31, 2014, the entire contents of which are incorporated herein by reference.

TECHNICAL FIELD

The present invention relates to an odor removal system, and more particularly, to a system for removing water soluble odor using an eco-friendly energy source and an effective microorganism.

BACKGROUND ART

Since the mid-1980's, studies on a biological processing technique among various methods for processing volatile organic compounds (VOCs) and odor which are released into the atmosphere has been earnestly performed in Europe and since the 1990's, a technique which removes the VOCs or odor from the contaminated air has become as a major issue in view of air pollution. According to the biological processing technique (Biofiltration), a reactor is filled with a filler including a microbial membrane and contaminated air passes through the filler to diffuse the contaminated material into the microbial membrane and oxidation-decompose the contaminated material by the microorganism, thereby purifying the contaminated air.

The biological removal technique has been known as a technique which is more economical and broadly applicable than a physicochemical processing technique of the related art such as an incineration method and an active carbon adsorption process which process the VOCs in terms of low cost equipment and low operating cost and is very useful in purifying contaminated air which is generated at a low concentration with a large amount.

Historically, as a biofilter in an early stage which has been used from the 1960's, a soil bed in which contaminated air is injected into a soil layer to be removed by soil adsorption and soil microorganism has been used. Even though an effect of removing 90% or more of VOCs and odor by the method is admitted, a large space is required for the soil bed and there is a technical problem of supplying uniform air into the soil layer in addition to high pressure loss.

Since the 1980's, as a filler of the biofilter, organic materials such as compost, peat, or a wood bark have been mainly used to process the odor and the VOCs. However, even though the organic filler has high removal efficiency due to high physical adsorption and good water retention capacity, the filler is decomposed by the microorganism and consolidated due to mineralization, so that air flow to the filler layer is not uniformly maintained.

Due to such a problem, the organic filler needs to be replaced or rearranged every year to maintain processing efficiency. Recently, in order to compensate for the problem of the organic filler, there is an attempt to mix the organic material such as compost, peat, or wood bark and an inorganic material such as plastic, pellet active carbon, or ceramic to improve the efficiency of the biofilter.

When the VOCs are processed by the biofilter of the related art which uses an organic matter as a filler, the microorganisms decompose the VOCs to use it as a carbon source so that the microorganisms are grown. Therefore, when the filler is attached thereto so that the microorganisms are overgrown, the overgrown microorganism (biomass) blocks an air gap of the filler which causes a pressure loss, so that processed air volume is reduced and processing efficiency is lowered, and thus entire removal efficiency is lowered. Also in a trickling air biofilter, an excessive pressure loss due to proliferation of overgrown surplus microorganism is caused. In order to solve the above-mentioned problem, an American inventor, Soriel et. al. (1997), invented a method of suppressing a microorganism from being grown using NaCl, but the method results in hindrance of growth and development of the microorganism and rapid reduction of the processing efficiency. Further, in a sulfur based component such as hydrogen sulfide, methyl sulfide, dimethyl disulfide, or methyl mercaptan or a nitrogen based component such as ammonia which is an inorganic odor material, blockage due to proliferation of excessive microorganisms does not matter. However, one of the most effective methods for increasing efficiency is to maintain a uniform microorganism concentration between an upper part and a lower part of a reactor.

It is very inefficient to provide a contaminated air purifying device which consumes high energy around an industrial complex where contaminated air is always discharged or in an area where other order is continuously distributed and generated and specifically, cost for frequently replacing a consumable filter is high.

Therefore, it is required to reduce soluble contaminated air which is discharged from the industrial complex or the area where other odor is continuously generated using an eco-friendly effective microorganism at low cost in a daily life and implement an eco-friendly self-independent device.

RELATED ART DOCUMENT

Patent Document

Korean Unexamined Patent Application Publication No. 10-2010-0100010

Korean Unexamined Patent Application Publication No. 10-2007-0116757

SUMMARY OF THE INVENTION

The present invention has been made in an effort to provide an eco-friendly heliostat odor removal system which is an ecofriendly system using solar heat as an energy source and efficiently reduces soluble order using an effective microorganism cultivation solution.

An exemplary embodiment of the present invention provides an eco-friendly heliostat odor removal system, including: a solar cell which collects sunlight to generate electricity; an effective microorganism activation and cultivation box which purifies inflow contaminated air using an effective microorganism cultivation solution accommodated in a housing; a sunlight tracker which rotates or moves the solar cell to track the sun in accordance with an altitude of the sun; a controller which controls the effective microorganism activation and cultivation box and the sunlight tracker; and a battery storing unit which stores the electricity generated in the solar cell.

When an internal temperature of the effective microorganism activation and cultivation box is higher than an effective temperature range, the controller may adjust the box by an air cooling method to be within the effective temperature range and when the internal temperature of the effective microorganism activation and cultivation box is lower than the effective temperature range, the controller may heat the box to increase the internal temperature to be adjusted within the effective temperature range.

The controller may flow air in the effective microorganism activation and cultivation box through an air compressing pump to maintain the effective temperature range by the air cooling method and heat the effective microorganism activation and cultivation box through a planar heating element to maintain the effective temperature range.

The controller may interwork a setting time in accordance with a timer setting with a position of the sun at that time to control the sunlight tracker. The sunlight tracker may include: a support which supports the solar cell; a base which fixes the support to a stable mechanism; and a sunlight tracking motor which moves the solar cell at an X axis and a Y axis along a movement passage of the sunlight with respect to an axis of the support.

The effective microorganism activation and cultivation box may include: a box type housing which is filled with the effective microorganism cultivation solution; an air inflow unit which is located at a bottom in the housing to flow the contaminated air therein; a contaminated air purifying unit in which a plurality of porous baffles spaced apart from each other at a regular interval at an upper edge of the air inflow unit is formed; a cylinder filter which is formed by a multi-stage disk located at an upper edge of the contaminated air purifying unit to adhere or adsorb impurities formed by dissolved contaminated air; and a discharging unit which outwardly discharges air generated at an upper edge of the box type housing.

In the air inflow unit, an inflow plate in which a plurality of pores is formed at an upper edge thereof to move the inflow air to the contaminated air purifying unit may be provided.

The air inflow unit may flow external contaminated air therein using a submerged pump which is connected to an inlet which is formed at a lower side of the housing to be provided in the housing.

The cylinder filter may include: a rotating rod formed at an upper edge of the housing; a plurality of circular disks which is fixed around the rotating rod as a central axis and spaced apart from each other at a regular interval along the rotating rod; and a motor which is connected to the rotating rod to be provided outside the housing and rotates the rotating rod.

According to the present invention, it is possible to use solar heat which is renewable energy, so that the system is an eco-friendly system and used for a small-sized night-time light or system driving, thereby reducing the energy.

Soluble contaminated air passes through an effective microorganism tank so that a part of the contaminated air is dissolved and reduced and a solid matter which causes odor as a by-product is decomposed by the effective microorganism to reduce odor.

As compared with a biofilter of the related art which uses the organic matter as a filler, problems such as nonuniform distribution of effective microorganism, pressure loss, and efficiency lowering due to overgrown microorganism are solved and the fluid is led to be smoothly and uniformly distributed, thereby improving purification efficiency.

BRIEF DESCRIPTION OF THE DRAWINGS

FIG. 1 is a functional block diagram illustrating a configuration of an eco-friendly heliostat odor removal system according to an exemplary embodiment of the present invention.

FIG. 2 is a view illustrating an example in which the heliostat odor removal system of FIG. 1 is configured.

FIG. 3 is a view illustrating an example in which a sunlight tracker is configured in the heliostat odor removal system of FIG. 1.

FIG. 4 is a schematic diagram of a configuration of an effective microorganism activation and cultivation box in the heliostat odor removal system of FIG. 1.

FIG. 5 is a view illustrating a shape of an inflow plate and a baffle in the effective microorganism activation and cultivation box of FIG. 4.

FIG. 6 is a view illustrating a configuration of a cylinder filter in the effective microorganism activation and cultivation box of FIG. 4.

FIG. 7 is a perspective view illustrating an overall configuration of an effective microorganism activation and cultivation box in the heliostat odor removal system of FIG. 1.

DETAILED DESCRIPTION

Advantages and characteristics of the present invention and a method of achieving the advantages and characteristics will be described by referring to exemplary embodiments described below in detail together with the accompanying drawings. As those skilled in the art would realize, the described embodiments may be modified in various different ways, all without departing from the spirit or scope of the present invention. The exemplary embodiments are provided to describe the technical spirit of the present invention in detail so as to be easily carried out by those skilled in the art. In the drawings, the exemplary embodiments of the present invention are not limited to an illustrated specific example but may be exaggerated for clarity. Like reference numerals designate like elements throughout the specification.

Unless particularly stated otherwise in the present specification, a singular form also includes a plural form. The word "comprise" and variations such as "comprises" or "comprising" used in the specification will be understood to imply presence or addition of one or more other components, steps, operations, and elements.

FIG. 1 is a functional block diagram illustrating a configuration of an eco-friendly heliostat odor removal system 1 according to an exemplary embodiment of the present invention, FIG. 2 is a view illustrating an example in which the heliostat odor removal system 1 of FIG. 1 is configured, and FIG. 3 is a view illustrating an example in which a sunlight tracker 15 is configured in the heliostat odor removal system 1 of FIG. 1.

Referring to FIG. 1, an eco-friendly heliostat odor removal system 1 according to an exemplary embodiment of the present invention includes a solar cell 10 which collects sunlight to generate electricity, an effective microorganism activation and cultivation box 50 which purifies inflow odor using an effective microorganism solution accommodated in a box type housing, a sunlight tracker 15 which rotates or moves the solar cell to track the sun in accordance with an altitude of the sun, and a controller 20 which controls the effective microorganism activation and cultivation box 50 and the sunlight tracker 15. Here, an eco-friendly self-independent device which supplies solar heat which is generated by controlling the sunlight tracker 15, that is, a heliostat to an effective microorganism tank to reduce soluble odor is implemented and a battery storing unit 16 which stores electricity generated from the solar cell 10 is further provided, so that the electricity stored in the battery storing unit 16 may be used at night when the sunlight is not obtained.

As illustrated in FIG. 2, the eco-friendly heliostat odor removal system 1 according to the exemplary embodiment of the present invention may be implemented such that a solar cell 10 plate is formed on a front surface facing the sun and major components such as the effective microorganism activation and cultivation box 50 are formed on a rear surface thereof. Since the power is generated in proportion to the area of the solar cell 10, it is desirable to form the solar cell over the entire front surface of the system to have a maximum area and form the remaining components on the rear surface. In this case, activation temperatures (hereinafter, referred to as effective temperatures) of the effective microorganism vary depending on the microorganism. However, since the effective microorganism activation and cultivation box is formed to be adjacent to the solar cell plate, the effective temperature is affected depending on whether to use the solar heat, which may influence the entire odor reducing effect. Therefore, in order to maintain the effective microorganism activation and cultivation box 50 at the effective temperature (for example, 30 to 40° C. in case of mesophile), when the solar heat is used, like day time, the controller 20 cools the effective microorganism activation and cultivation box 50 by an air cooling method which flows air into the effective microorganism activation and cultivation box 50 through an air compressing pump 30 in consideration of the influence of temperature rise to maintain the effective temperature range. In contrast, when the solar heat is not used like the nighttime, the controller 20 heats the effective microorganism activation and cultivation box 50 through a planar heating element 40 in consideration of a temperature drop to maintain an effective temperature range.

As described above, when an internal temperature of the effective microorganism activation and cultivation box 50 is higher than the effective temperature range, the controller 20 cools the effective microorganism activation and cultivation box 50 through the air compressing pump 30 to adjust the temperature to be within the effective temperature range and when the internal temperature of the effective microorganism activation and cultivation box 50 is lower than the effective temperature range, the controller 20 heats the effective microorganism activation and cultivation box 50 using the planar heating element 40 to increase the internal temperature, thereby adjusting adjust the temperature to be within the effective temperature range. Further, the effective microorganism area of the effective microorganism activation and cultivation box 50 is mainly configured by an aerobic effective microorganism (EM) area in which air is required to aerobically respire and an anaerobic EM area in which air is not required to anaerobically respire. Therefore, the air is injected in the aerobic EM area through the air compressing pump 30 to optimize a cooling effect and the planar heating element 40 is formed in the anaerobic EM area to optimize a heating effect to distinguish the aerobic EM area and the anaerobic EM area in terms of utilizing a space to double the effect of adjusting the temperature.

The eco-friendly heliostat odor removal system 1 according to the exemplary embodiment of the present invention includes the sunlight tracker 15 which controls a direction of the solar cell 10 in accordance with a movement route of the sun. Referring to FIG. 3, the system is configured such that two sunlight modules in which the solar cell 10 plate on the front surface and the effective microorganism activation and cultivation box 50 on the rear surface are formed track the sunlight. In this case, the sunlight tracker 15 includes a support 11 which supports the sunlight module, a base 13 which fixes the support to stable equipment, and a sunlight tracking motor 12 which moves the sunlight tracker to an X axis or a Y axis along the movement route of the sunlight with respect to an axis of the support 11. In this case, the controller 20 which controls the sunlight tracker 15 may control the sunlight tracker 15 in accordance with a time of an internal timer, for example, simply in accordance with the route of the sun which rises from the east in the morning and sets in the west in the evening. As described above, the controller 20 interworks a rough time in accordance with a timer setting with a position of the sun at that time to control the direction of the solar cell plate or interworks a sensor value which is detected by using a thermal sensor with the position of the sun to control the direction of the solar cell plate.

FIG. 4 illustrates the effective microorganism activation and cultivation box 50 of the eco-friendly heliostat odor removal system 1 of FIG. 1, in which FIG. 4A is a front view and FIG. 4B is a side view. FIG. 5 is a view illustrating a shape of an inflow plate 250 and a baffle 310 used in the effective microorganism activation and cultivation box 50 of FIG. 4, FIG. 6 is a view illustrating a configuration of a cylinder filter used in the effective microorganism activation and cultivation box 50 of FIG. 4, and FIG. 7 is a perspective view illustrating an overall configuration of an effective microorganism activation and cultivation box 50 of FIG. 4.

As illustrated in FIGS. 4 and 7, the effective microorganism activation and cultivation box 50 has a box shape which is filled with an effective microorganism cultivation solution and includes an air inflow unit 200 which is located at a bottom in the box type housing 100 to flow the odor therein, a contaminated air purifying unit 300 in which a plurality of porous baffles 310 is provided at an upper edge of the air inflow unit 200 to be spaced apart from each other with a regular interval, a cylinder filter 400 which is formed of a multi-stage disk 410 which is located on an upper edge of the contaminated air purifying unit 300 to adhere or adsorb impurities formed by the dissolved odor, and a discharging unit 500 which discharges air generated at the upper edge of the box type housing to the outside.

The present invention as described above suggests an odor removal system which fills the box type housing 100 with the effective microorganism solution and then makes the odor generated from the industrial site or various odor discharging areas flow in through the air inflow unit 200 at the lower edge, purifies the soluble odor gas such as volatile gas (for example, ammonia) by the biological purifying action while the soluble odor gas passes through the contaminated air purifying unit 300 and the cylinder filter 400 as the soluble odor gas rises, and then discharges the purified air or gas through the discharging unit 500 at the top.

The exemplary embodiment of the present invention provides an odor purifying device in which the odor passes through the plurality of porous baffles 310 spaced apart from each other in a vertical direction in accordance with the rise of the odor to prolong or delay a gas-liquid contact time so that the odor sufficiently contacts with the effective microorganism solution to accelerate the microorganism cultivation and purification and by a secondary filtering action which filters the by-product or various impurities generated while the soluble odor is dissolved by a cylindrical cylinder filter 400 in which a plurality of disks 410 pivots at the upper edge of the housing 100, the odor is more efficiently purified, which is different from a simple biofilter through a carrier of the related art.

As compared with a biofilter of the related art which uses the organic matter as a filler, the exemplary embodiment of the present invention provides a system which does not cause problems such as nonuniform distribution of effective microorganisms, pressure loss, and efficiency lowering due to overgrown microorganism and the fluid in which the effective microorganism solution and the odor are mixed is led to be smoothly and uniformly distributed, thereby improving purification efficiency.

As illustrated in FIG. 5, the air inflow unit 200 corresponds to the external contaminated air inflow unit 200 which is formed at a lower edge of the box housing 100. In the air inflow unit 200, an inlet through which the external odor is flown therein is formed at a lower side of the box housing 100 and a submerged pump 210 which is connected to the inlet is provided therein at the lower edge of the box housing 100 to efficiently flow the external odor therein.

The box housing 100 is filled with the effective microorganism solution in order to biologically purify the air and the air flown from the air inflow unit 200 forms bubbles and moves to the upper end of the effective microorganism solution due to specific gravity of the bubbles. During this movement, a microorganism in the odor which is dissolved in the soluble gas and the effective microorganism solution or present in the effective microorganism solution decomposes some of gas materials, thereby purifying the odor in accordance with the rising gas.

In the air inflow unit 200, the submerged pump is driven so that the external odor may be rapidly flown and the air may move while the flow of the air is leaned to one side. Therefore, in order to disperse and uniformly distribute the leaned air and upwardly distribute the air, an inflow plate 250 having a plurality of pores is provided between the contaminated air purifying unit 300 and the air inflow unit 200.

In order to perform a function of covering the air inflow unit 200 and serve as a passage which uniformly upwardly moves the odor which is nonuniformly distributed and moves in the air inflow unit 200, in the inflow plate 250, a plurality of pores is formed in a flat plate to secure a movement passage of the odor and lead the odor to be uniformly and upwardly distributed and spread, so that efficient gas-liquid contact is generated over a wide area to increase the purifying efficiency.

At the upper edge of the air inflow unit 200, a contaminated air purifying unit 300 which secures a space and prolongs the air-liquid contact time to increase the purifying efficiency in order to purify the odor through the effective microorganism solution is provided. The contaminated air purifying unit 300 is formed such that a plurality of porous baffles is alternately attached on both sides of the housing 100 to be parallel to each other at a regular interval in a vertical direction.

As described above, a structure in which the porous baffles 310 are provided to be spaced apart from each other with a regular interval in a vertical direction is suggested in the exemplary embodiment of the present invention because the bubbles of the contaminated air which passes through the inflow plate 250 to rise in the air inflow unit 200 at the lower edge of the housing 100 rapidly move upwardly and the rapid movement shortens the reaction or contact time with the effective microorganism solution to lower the purifying efficiency, and therefore, the porous baffles 310 in which a plurality of pores through which the contaminated air passes is formed is spaced apart from each other at a regular interval in a vertical direction, so that the movement of the contaminated air is delayed to increase the air-liquid contact time and the baffles 30 uniformly distribute and spread the contaminated air through the pores, thereby increasing the air-liquid contact area to increase efficiency of the microorganism or the chemical reaction.

The plurality of baffles 310 may be mounted on the entire cross-section of the box housing 100 like the inflow plate 250 at the lower edge to allow the odor to pass through the pores or as illustrated in FIG. 7, a cross-section of the baffle 310 is made to be smaller than a cross-section of the box housing 100 to mount the baffle 310 on one surface of the box housing 100 and mount the baffle 310 on an opposite surface of the box housing at an upper edge thereof so that the baffles 310 are mounted with a predetermined interval in a zigzag manner in order to leave an available space, thereby smoothly moving the contaminated air.

FIG. 5 illustrates a shape of the inflow plate 250 and the porous baffle 310 which are applied to the exemplary embodiment of the present invention. As illustrated in FIG. 5, the inflow plate 250 and the porous baffles 310 have a structure in which a plurality of pores is formed on a plate having a predetermined area to lead the contaminated air which rises through the pores to be smoothly moved with a uniform distribution. Materials of the inflow plate 250 and the baffles 310 may be formed of non-metal material such as plastic, glass, or a polymer, rather than the metal material because the inflow plate and the baffles may be easily corroded by an acidic solution which is generated in reaction with the various stink contaminated air and the effective microorganism solution.

As described above, in the related art, the bubble of the contaminated air rapidly rises, so that the sufficient gas-liquid contact time with the effective microorganism solution is not secured. Therefore, the purification efficiency is lowered. However, in the present invention, the plurality of porous baffles 310 which is provided in the contaminated air purifying unit 300 located at the middle part of the box housing 100 delays the flow of the odor bubbles and prolongs the gas-liquid contact time, thereby increasing efficiency of the purification.

As illustrated in FIGS. 4 and 6, a cylindrical cylinder filter 400 which is formed of a multi-stage disk 410 is provided at the upper edge of the contaminated air purifying unit 300. The cylinder filter provides a device which after passing through a sufficient reaction process with the effective microorganism solution in the contaminated air purifying unit 300, performs a secondary filtering process of filtering the by-product or the impurity in which the soluble odor is dissolved or microorganism reaction is not sufficiently performed to sufficiently expose the odor to the effective microorganism solution to accelerate purification.

The cylinder filter may be configured by a rotating rod 450 which is formed at the upper edge of the box housing 100 in a horizontal direction, a plurality of circular disks 410 which is provided to be fixed around the rotating rod 450 as a central axis and is spaced apart from each other with a regular interval along a length direction of the rotating rod 450, and a motor which is connected to the rotating rod 450 to be provided at an outside of the cultivation box 100 and rotates the rotating rod 450.

That is, the cylinder filter 400 is a device which is configured by the rotating rod 450, the multi-stage disk 410, and the rotating motor. The rotating rod 450 is a rod type bar which traverses the sides of the housing of the cultivation box 100 to be formed at the upper edge and serves as a rotation axis. In the rotating rod 450, the plurality of circular disks 410 is mounted in the length direction with a regular interval around the rotating rod 450. The rotation motor is connected to one side of the rotating rod 450 to rotate the rotating rod 450, so that the cylinder filter 400 efficiently attaches various by-products during the process of dissolving the soluble odor to perform the secondary filtering process.

The cylinder filter rotating structure serves to smoothly and upwardly move the fluid of the contaminated air purifying unit 300 and rotates the fluid at a rotation speed of approximately 5 RPM or slower to naturally attach the by-product onto the multi-stage disk 410. This is because the by-product and chemical complex dissolved in the effective microorganism solution may be easily attached on a surface of the cylinder of the cylindrical disk 410 having a large surface area. Further, the effective microorganism oxidizes and decomposes the organic matter attached on the surface of the plurality of disks 410 to perform the secondary purifying function of the solution.

The discharging unit 500 is provided with an exit at the upper edge of the housing 100 and serves as a passage which discharges the purified contaminated air to the outside formed in the upper space which is filled with the effective microorganism solution in the housing 100. A mesh filter which physically removes an impurity of general duty is provided in the discharging unit 500 to discharge more clean and purified air to the outside. Further, an inhalation air pump is mounted in the discharging unit 500 to efficiently discharge the purified contaminated air which is generated at the upper edge of the cylinder filter.

In the above description, even though the present invention has been illustrated and described with respect to a specific exemplary embodiment, various modifications and changes become apparent to those skilled in the art without departing from the spirit and the scope of the invention represented in the claims.

What is claimed is:

1. An eco-friendly heliostat odor removal system, comprising:
   a solar cell which collects sunlight to generate electricity;
   a microorganism activation and cultivation box which purifies inflow contaminated air using a microorganism cultivation solution;
   a sunlight tracker which rotates or moves the solar cell to track the sun in accordance with an altitude of the sun;
   a controller which controls the microorganism activation and cultivation box and the sunlight tracker; and
   a battery storing unit which stores the electricity generated in the solar cell, wherein the microorganism activation and cultivation box includes:
   a housing which is filled with the microorganism cultivation solution;
   an air inflow unit which is located at a bottom in the housing to flow the contaminated air therein;
   a contaminated air purifying unit in which a plurality of porous baffles spaced apart from each other at a regular interval at an upper edge of the air inflow unit is formed;
   a cylinder filter which is formed by a multi-stage disk located at an upper edge of the contaminated air purifying unit to adhere or adsorb impurities formed by dissolved contaminated air; and
   a discharging unit which outwardly discharges air generated at the upper edge of the housing.

2. The system of claim 1, wherein when an internal temperature of the microorganism activation and cultivation box is higher than an effective temperature range, the controller adjusts the microorganism activation and cultivation box by an air cooling method to be within the effective temperature range and when the internal temperature of the microorganism activation and cultivation box is lower than the effective temperature range, the controller heats the microorganism activation and cultivation box to increase the internal temperature to be adjusted within the effective temperature range.

3. The system of claim 2, wherein the controller flows air in the microorganism activation and cultivation box through an air compressing pump to maintain the effective temperature range by the air cooling method and heats the microorganism activation and cultivation box through a planar heating element to maintain the effective temperature range.

4. The system of claim 1, wherein in the air inflow unit, an inflow plate in which a plurality of pores is formed at an upper edge thereof to move the inflow air to the contaminated air purifying unit is provided.

5. The system of claim 4, wherein the air inflow unit flows external contaminated air therein using a submerged pump which is connected to an inlet which is formed at a lower side of the housing to be provided in the housing.

6. The system of claim 1, wherein the cylinder filter includes:
   a rotating rod formed at an upper edge of the housing;
   a plurality of circular disks which is fixed around the rotating rod as a central axis and spaced apart from each other at a regular interval along the rotating rod; and
   a motor which is connected to the rotating rod to be provided outside the housing and rotates the rotating rod.

7. The system of claim 1, wherein the controller interworks a setting time in accordance with a timer setting with a position of the sun at that time to control the sunlight tracker.

8. The system of claim 7, wherein the sunlight tracker includes:
   a support which supports the solar cell;
   a base which fixes the support to a stable mechanism; and
   a sunlight tracking motor which moves the solar cell at an X axis and a Y axis along a movement passage of the sunlight with respect to an axis of the support.

* * * * *